US006510818B2

(12) United States Patent
Barney et al.

(10) Patent No.: US 6,510,818 B2
(45) Date of Patent: Jan. 28, 2003

(54) DRUG DELIVERY MASK FOR ANIMALS

(75) Inventors: Brian Barney, Bishops Stortford (GB); Esther Perea-Borobio, London (GB)

(73) Assignee: Norton Healthcare, Ltd., London (GB)

(*) Notice: Subject to any disclaimer, the term of this patent is extended or adjusted under 35 U.S.C. 154(b) by 0 days.

(21) Appl. No.: 09/861,979

(22) Filed: May 21, 2001

(65) Prior Publication Data

US 2002/0073934 A1 Jun. 20, 2002

Related U.S. Application Data

(60) Provisional application No. 60/207,614, filed on May 26, 2000, and provisional application No. 60/204,792, filed on May 16, 2000.

(51) Int. Cl.[7] .......... A62B 18/02
(52) U.S. Cl. .......... 119/831; 128/203.29
(58) Field of Search .......... 119/420, 831; 128/200.14, 200.18, 203.29, 206.21, 206.24, 206.28; D24/110.1, 110.4

(56) References Cited

U.S. PATENT DOCUMENTS

| | | | | |
|---|---|---|---|---|
| 2,609,235 A | * | 9/1952 | Reimann | 128/200.14 |
| 2,749,910 A | | 6/1956 | Faulconer, Jr. | 128/29 |
| D216,493 S | * | 1/1970 | Miczka | 128/206.28 |
| 3,491,755 A | * | 1/1970 | Barghini et al. | 128/201.13 |
| 4,002,167 A | | 1/1977 | Rambosek | 128/205 |
| 4,384,577 A | * | 5/1983 | Huber et al. | 128/206.19 |
| 4,546,768 A | * | 10/1985 | Ferierabend | 128/200.16 |
| 5,121,745 A | | 6/1992 | Israel | 128/202.28 |
| 5,660,174 A | | 8/1997 | Jacobelli | 128/206.24 |
| 5,809,996 A | | 9/1998 | Alldredge | 128/200.23 |
| 5,954,049 A | * | 9/1999 | Foley et al. | 128/200.23 |
| 6,347,629 B1 | * | 2/2002 | Braithwaite | 128/200.18 |
| 6,371,111 B1 | * | 4/2002 | Ohki et al. | 128/203.15 |

FOREIGN PATENT DOCUMENTS

| | | | | |
|---|---|---|---|---|
| DE | 29907507 U | | 8/1999 | A61D/7/04 |
| GB | 2 110 543 A | * | 12/1981 | A61M/15/00 |
| JP | 405123398 A | * | 5/1993 | A61M/11/00 |

* cited by examiner

*Primary Examiner*—Charles T. Jordan
*Assistant Examiner*—Kimberly S. Smith
(74) *Attorney, Agent, or Firm*—McDermott, Will & Emery

(57) ABSTRACT

An animal mask for removable fitment to the appropriate portion of the head of an animal such as the front of the head or over one nostril for the effective delivery of drugs or medicaments, for pulmonary or nasal absorption. The rings of the mask are nestable, forming a succession of monotonically decreasing sized telescopable rings from a largest ring to a smallest ring to form a relatively flexible skirt. An animal interface adapter extends from the largest ring and is adapted to establish a substantial seal between the animal interface adapter and the face of an animal. The animal mask is collapsible to permit use in a full or partially open state, and to permit easy and convenient transport in a collapsed or closed state.

37 Claims, 13 Drawing Sheets

DRUG DELIVERY MASK FOR ANIMALS

This application claims benefit of Prov. No. 60/204,792 filed May 16, 2000 and prov. No. 60/207,614 filed May 26, 2000.

BACKGROUND OF THE INVENTION

1. Field of the Invention

The invention relates to the delivery of drugs to animals, and more particularly to devices for enabling the delivery of drugs or medicaments to animals for pulmonary or nasal absorption via the mouth and or nose.

2. Summary of the Related Art

In many circumstances, it is desired to deliver a drug or a medicament to an animal, and in particular a mammal, such as a human, a dog or a horse, for pulmonary or nasal absorption. Direct application, such as by a spray or aerosol delivery device, or a dry powder delivery device, is difficult due to movements of the animal. To enable such application of medicaments in the prior art, an elongated, generally cup-shaped "mask" is often provided, having a relatively large open base end for fitment over an animal's nostril or muzzle and having a medicament administration port opposite that base end. Typically the mask is made out of a semi-rigid material (eg., sheet polycarbonate) and is provided in various sizes for use with different sized animals.

In use in the prior art, an appropriate sized mask is selected, and the open base end is positioned over the animal's nostril or muzzle, preferably with a friction fit at the open base end. The size of the open end is such that at least a rough seal is established between the open end of the mask and the animal's nostril or muzzle. When the mask is so positioned, medicament is delivered at the medicament administrative port, for example by spray, aerosol delivery device, or dry powder medicament delivery device, either breath-activated or user-driven. As the animal breathes, the medicament is drawn into one (or both) nostril(s), or in the mouth and into the lungs or the nasal passages.

This mask-type administration of medicaments has proven to be a generally effective method for medicament delivery. However, there are inconveniences and difficulties associated with the prior art masks. More particularly, because of the semi-rigid structure of such masks, the masks are bulky and take up significant volume when carried around by a veterinarian, or other provider. Moreover, the semi-rigid structure of such masks makes it necessary to provide a set of various sized masks in order to be able to provide masks for correspondingly sized animals. In addition, because of the "rough" nature of the seal provided by the semi-rigid material of the conventional masks, many of those masks are provided with tubes, and the like, for insertion deep into the animal's nostrils. The latter type of mask is particularly difficult to clean making it difficult to use it for more than one animal at a time without cross-contamination.

Therefore, there is a need for an improved mask for delivering drugs to animals for pulmonary or nasal absorption via the mouth and/or nose. Such improved mask should be (a) collapsible to a relatively small volume form for ease and convenience in transport; (b) adaptable for use with different sized animals; and (c) easily cleaned, to permit re-use with the same or different animals.

BRIEF SUMMARY OF THE INVENTION

The present invention is a drug or medicament, delivery device for fitment to the appropriate portion of the head of the animal such as the front of the head or over one nostril for the effective delivery of drugs or medicaments, for pulmonary or nasal absorption. The device is in the form of a mask. The mask is collapsible to permit use in a full or partially open state, and to permit easy and convenient transport in a collapsed or closed state. In a preferred form, the mask of the invention is particularly adaptable to accommodate size variation in animals.

The drug delivery mask of the invention is adapted for removable fixture to the appropriate portion of the head of the animal such as the front of the head (i.e, a portion of the face), the nostril or the muzzle. The mask includes two or more telescopable sections, which are coupled together. Each section includes a relatively inflexible ring defining an associated first contour, and each has a relatively flexible skirt extending from its ring to a distal edge. The distal edge of the skirt defines an associated second contour. The rings of the mask are nestable, forming a succession of monotonically decreasing sized rings from a largest ring to a smallest ring. Preferably, each ring fits inside the next larger ring in the succession, although in some forms two adjacent rings in the succession may be same size, and may not nest with each other. The second contour of a skirt of each ring in the succession, is substantially the same as, and is joined to, the first contour of the next ring of the succession. The various joined sections may be formed (such as by molding) as a unitary structure.

The present invention is intended for use with any animal which may experience the benefits of the invention. Foremost among such animals are those which are difficult to control or cannot be made to cooperate in the delivery of drugs or medicaments via conventional delivery devices. Hence the term "animal" is used to designate patients such as infants, children, physically or mentally disabled patients, as well as any other animal (e.g., a dog, a cat or a horse).

An airborne medicament interface adapter extends from the skirt of the smallest ring. The medicament interface adapter is adapted to couple that skirt to a medicament dispenser. Preferably, the medicament dispension is breath-activated but may be user (e.g., care giver) actuated. The medicament dispenser may be in the form of a dry powder medicament dispenser, or in aerosol dispenser. Alternatively, a user-actuated spray dispenser may be used.

The mask also includes an animal interface adapter extending from the largest ring. The animal interface adapter is adapted to provide a substantial (although not necessarily complete) pneumatic seal between the animal interface adapter and the appropriate portion of the head of the animal (e.g., the front of the head of a small child, the nostril or the muzzle of any animal such as cats, dogs or horses). By way of example, the animal interface adapter may be in the form of a thin or tapered flexible sheet, which when pressed against the area around the appropriate portion of the head, forms at least a rough seal. As a further example, the animal interface adapter may be in the form of a stretchable, nominally conic-frustrum shaped elastic sheet, extending from the largest ring. In the elastic form, the sheet may be stretched as the largest ring is moved over the nostril or muzzle of the animal. In some forms, an elastic or otherwise adjustable strap extends from the animal interface adapter, where the strap may be placed around the back of an animal's head to secure the mask in place.

In a preferred form of the inventions, the sections of the mask are formed by molding as a unitary structure, made from one of the group consisting of a thermoplastic elastomer, high density polyethylene, low density polyethylene, polypropylene and silicone rubber. One of skill will appreciate that any material or method available in the art can be utilized in carrying out the invention. However, preferred materials methods are described. Materials, reagents and the like to which reference is made in the following description and examples are obtainable from commercial sources, unless otherwise noted.

The rings may be circular, elliptical or some other closed shape. By way of example, the respective rings may have a C-shaped cross-section, to impart a relatively inflexible characteristic, with its associated skirt extending from one end of the C and the distal edge of the skirt from the next ring being joined to the other end of the C. The skirts may be a material to impart a relatively flexible characteristic. Various dimensions and geometries may be used in keeping with the invention.

BRIEF DESCRIPTION OF THE DRAWINGS

For a fuller understanding of the nature and the objects of the invention, reference should be made to the following detailed description and the accompanying drawings in which the reference numerals refer to like elements and in which.

DESCRIPTION OF THE PREFERRED EMBODIMENTS

Figure 1:
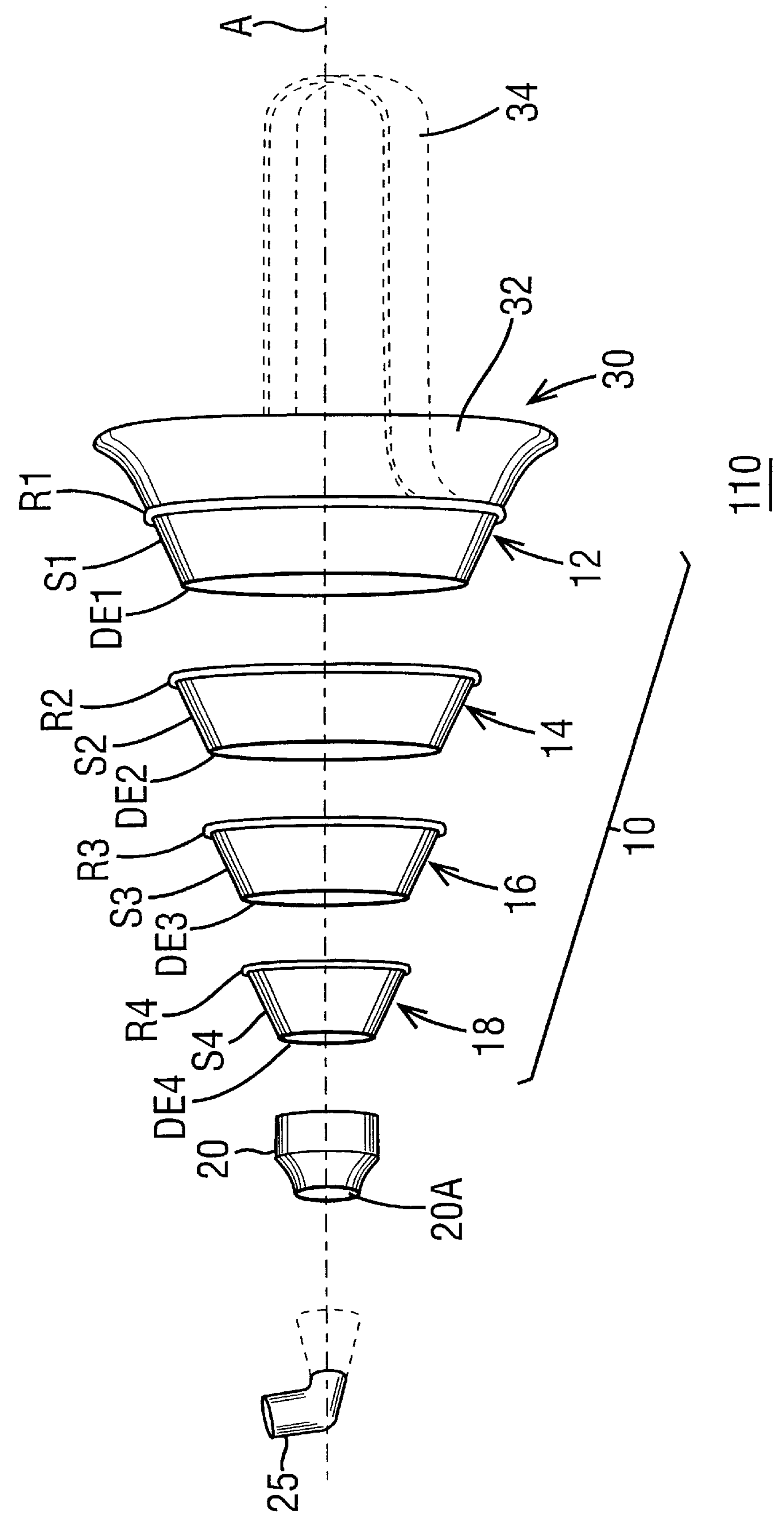
FIG. 1 shows in exploded diagrammatic form, a drug delivery mask in accordance with the invention.

An exemplary drug delivery mask 110 embodying the present invention for use with dogs, horses, humans and other mammals is shown in diagrammatic form in FIG. 1. The mask 110 is shown in exploded form to illustrate the various components which in a fully formed mask are a unitary structure.

Figure 2A:
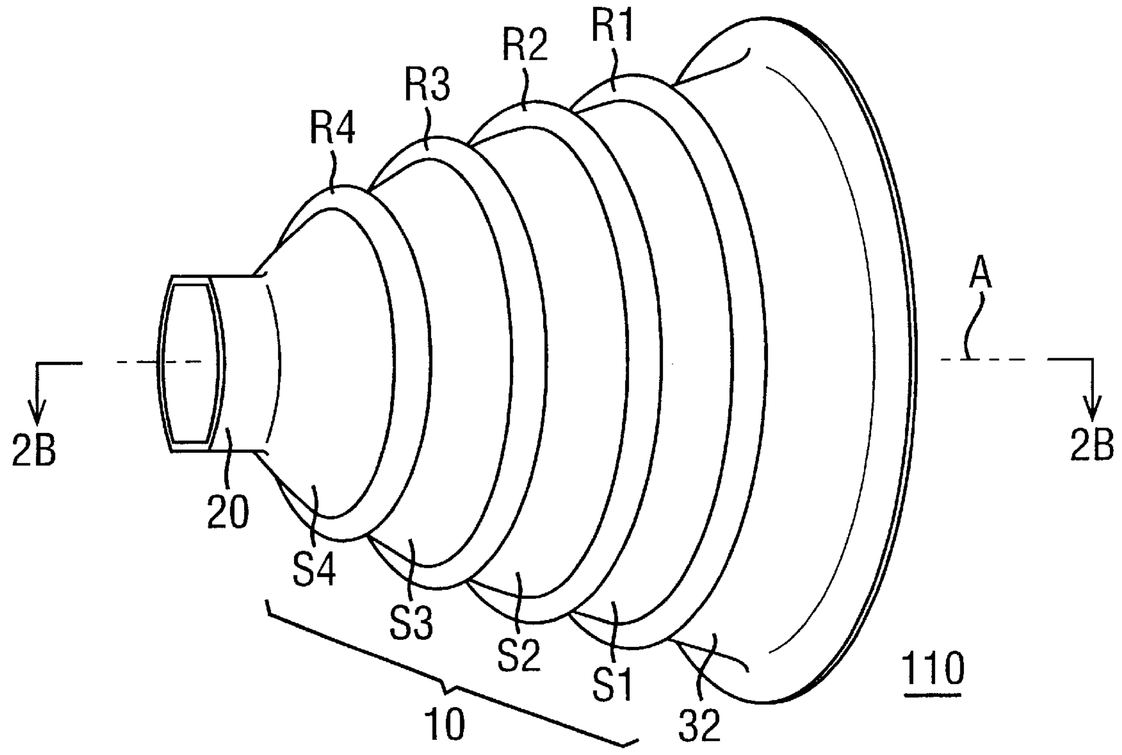
FIG. 2A shows in diagrammatic form, an exemplary drug delivery mask of the invention, in an open state as it might be deployed over the head of an animal.
Figure 2B:
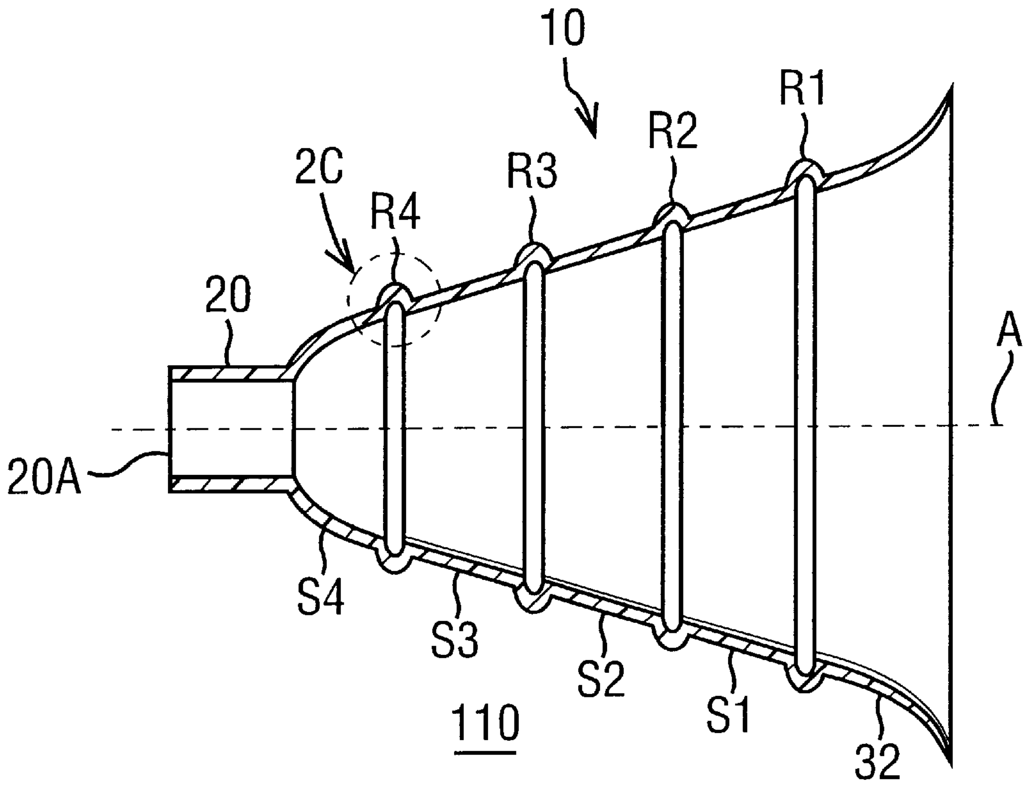
FIG. 2B shows a sectional view of the mask of FIG. 2A along the lines 2A—2A.
Figure 3A:
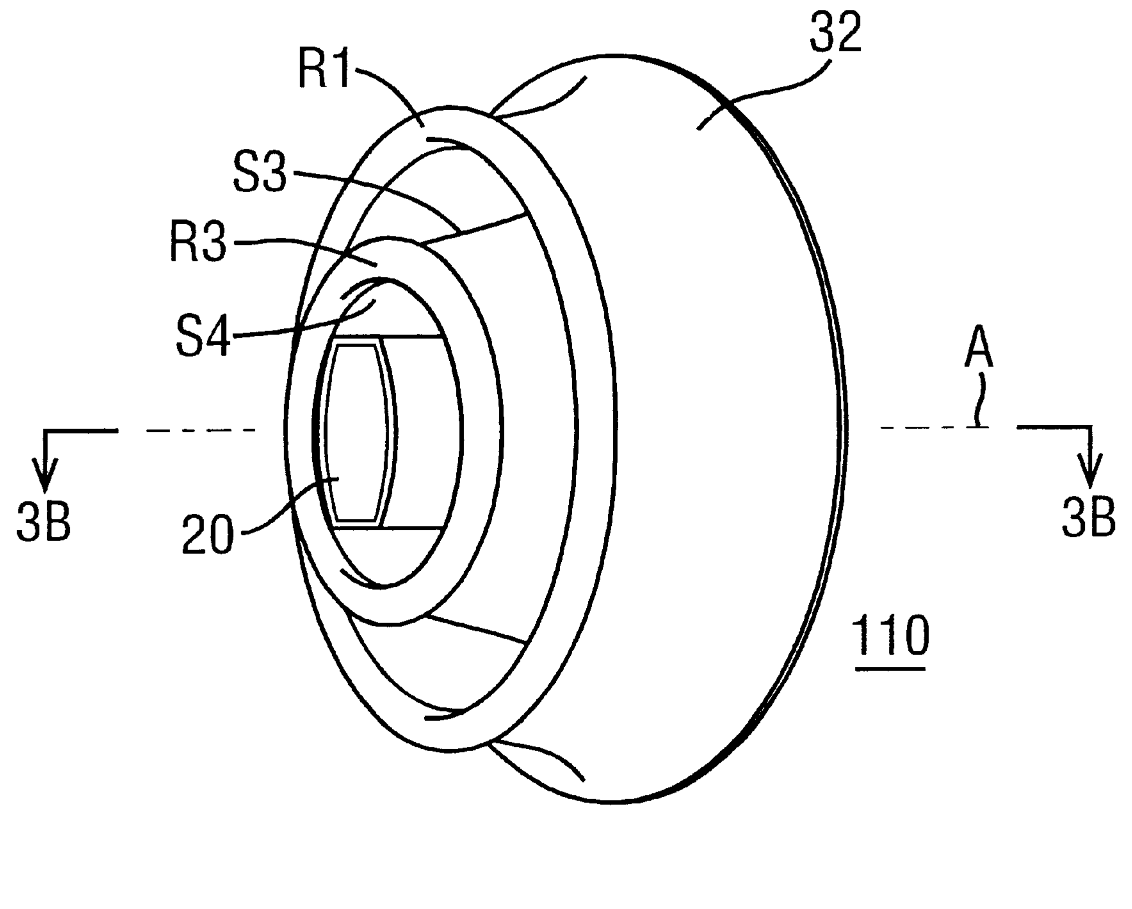
FIG. 3A shows in diagrammatic form, the mask of FIG. 2, in a small volume, closed, or collapsed, form, ads it might be configured for storage or transport.
Figure 3B:
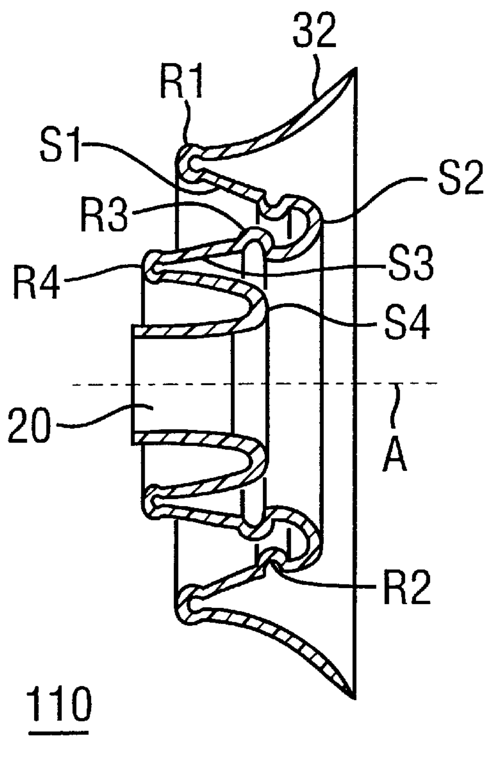
FIG. 3B shows a section view of the mask of FIG. 3A along the lines 3A—3A.

A similar mask 110 is shown in FIGS. 2A, 2B, 3A and 3B. The mask 110 is a unitary structure. FIGS. 2A and 2B show the mask 110 in an open state, having a bell or similar shape, as it might be deployed over the nostril or muzzle of an animal in use. FIGS. 3A and 3B show mask 110 in a small volume, closed, or collapsed, state, as it might be configured to permit convenient transport or storage.

As shown in exploded form in FIG. 1 and in a unitary form in FIGS. 2A, 2B, 3A and 3B, the mask 110 includes a sleeve 10 extending along a central axis “A” between an airborne medicament interface 20 and an animal interface adapter 30.

The sleeve 10 includes four sections 12, 14, 16, and 18 extending along the central axis “A”. Each of the sections includes a relatively inflexible ring Ri defining an associated first contour, having a relatively flexible skirt Si extending therefrom to a distal edge DEi. The distal edge DEi defines a second contour, where “i”=1, 2, 3, . . . The rings R1, R2, R3, R4 of assemblies 12, 14, 16, and 18 form a monotonically decreasing succession of circular rings, from the largest ring R1 to the smallest ring R4. The succession is monotonic in that the individual rings in the succession are successively smaller, although in other embodiments, a ring may be the same (but not larger than) its next (in the succession) neighbor. Moreover, as shown, each ring in the illustrated embodiment is sufficiently larger than the next ring (in the succession) so that the smaller ring fits within, i.e., nests, with its neighbor. The distal edge DEi of each ring Ri is the same size as the contour defined by next smaller ring R in the succession; that is, DE1 is the same size as R2, DE2 is the same size as R3 and DE3 is the same size as R4. The distal edge of each skirt of sections 12, 14, and 16 is joined to the ring of the respective one of neighboring sections 14, 16, and 18.

In general, the mask is made from a soft, supple material having good memory. By way of example, the rings and skirts are made from plastics, for example, one of the group consisting of thermoplastic elastomers, high density polyethylene, low density polyethylene, polypropylene, and silicone rubber. By way of example, the thermoplastic may be of the type sold under the trademarks Elastolene, Evoprene, Pebax or Santoprene. With such materials, the mask 110 is easily washable for use with a number of animals in kennels or stables, with no risk of cross-contamination. It is also envisioned that the mask can be made from materials other than plastic, such as a rubber, synthetic rubber, silicone, soft nylons, or can include support materials, such as fibers or a cloth material, such as canvas, contained within the plastic or rubber to provided strength and durability.

Figure 2C:
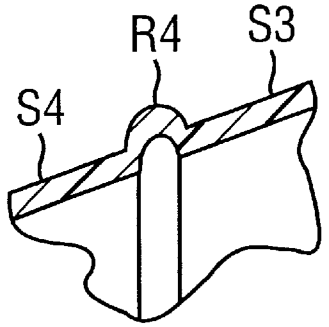
FIG. 2C shows an enlarged sectional view of a portion of the mask contained in circle 2C of FIG. 2B.

In a preferred form, the mask 110 is a unitary structure formed by molding for example, high density polyethylene. In the illustrated embodiment, the thickness of the material forming mask 110 is in the range 0.12–0.15 cm, although other thicknesses may be used depending on the desired flexibility. The rings are circular and are relatively inflexible. As shown best in FIG. 2C, the rings are C-shaped in cross-section having an outer diameter 0.5 cm. The skirt for a ring extends from one end of the C and the distal edge of the skirt of the next larger ring is coupled to the other end of the C. Other forms of rings may be used, for example, solid rings having a circular or ellipitcal or other shaped cross-section. The skirts are relatively flexible. The adjacent ones of sections 12, 14, 16 and 18, are joined together DE1-to-R2, DE2-to-R3, and DE3-to-R4. Preferably, the entire structure 110, is formed in a single step with a molding process. The molding process may comprise rotational molding, blow molding or injection molding, for example. The mask 110 can alternatively be made by vacuum forming. Many acceptable methods of forming the mask 110 can be used.

The airborne medicament interface 20, which is generally cylindrical, extends from the distal end DE4 of skirt S4 of section 14. The interface 20 may be formed from the same material as the skirt S4 or another compatible material. Preferably, the interface 20 is integral with, and merely an extension of the skirt S4. The end 20A of interface 20 opposite to the end joined to skirt S4 is shaped to couple to, or receive, an external aerosolizing medicament dispenser 25. As shown in FIG. 1, the dispenser 25 is schematically represented as an aerosol dispenser, with its effluent plume directed to the interior of interface 20. In various embodiments, the dispenser 25 may be a metered dose breath-actuated or user—(e.g., veterinarian) operated inhaler and may be a dry powder or aerosol dispenser. Preferably, the device 25 includes an output structure which directs airborne medicaments to the interior of mask 110.

The animal interface adapter 30 extends along axis “A” from ring R1. In the embodiments illustrated, the interface 30 is in the form of a tapered sheet 32. In other embodiments, the sheet 32 can be in the form of a conic-frustrum shaped shroud made of an easily stretchable elastic material. The sheet 32 is adapted to provide a substantial (although not necessarily total) pneumatic seal between ring R1 and the nostril or muzzle of an animal. As illustrated in phantom in FIG. 1, the interface 30 may optionally include a stretchable elastic or otherwise adjustable strap 34 extending from or near opposite sides of ring R1, to permit secure fixture of mask 110 to the head of an animal.

With the configuration of mask 110 as shown, where the extension assemblies 12, 14, 16, 18 and interfaces 20 and 30 form a unitary structure, the mask 110 is usable in two states; a first or open state where the various sections 12, 14, 16, 18 are “telescoped” out to form a mask for fitment to an animal, and in a second or collapsed state to establish a low volume structure convenient for storage or transport. FIGS. 2A and 2B illustrate the open state for mask 110 and FIGS. 3A and 3B illustrate the collapsed state for mask 110.

Figure 3C:
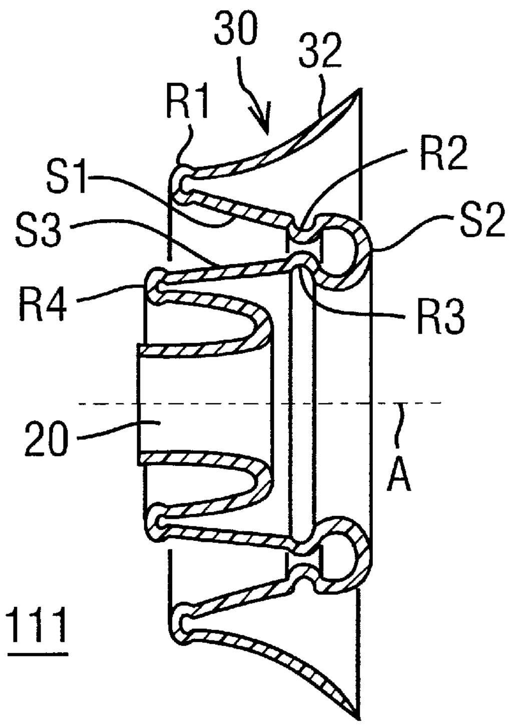
FIG. 3C shows a section view, similar to FIG. 3B, of a portion of another drug delivery mask in accordance with the invention.

In addition, the mask 110 is also usable in an intermediate or partially open state, wherein at least two of the various sections are “telescoped” out to form a mask for fitment to an animal and where one of the rings forms the necessary seal to the animal. In this way, a single mask may accommodate several sizes of animals. FIG. 3C shows another mask 111 according to the present invention, especially adapted for use in an intermediate state. The mask 111 of FIG. 3C is similar to the mask 110 of FIGS. 1 through 3, such that elements that are the same have the same reference numerals. The skirts S1 and S3 of the mask 111 of FIG. 3C, however, are provided with a greater length (along the axis “A”), such that when the mask 111 is in an intermediate or partially open state the folded skirt S2 extends beyond the animal interface 30.

Figure 4A:
FIG. 4A shows a mask of the invention positioned over the nostril of an animal.
Figure 4B:
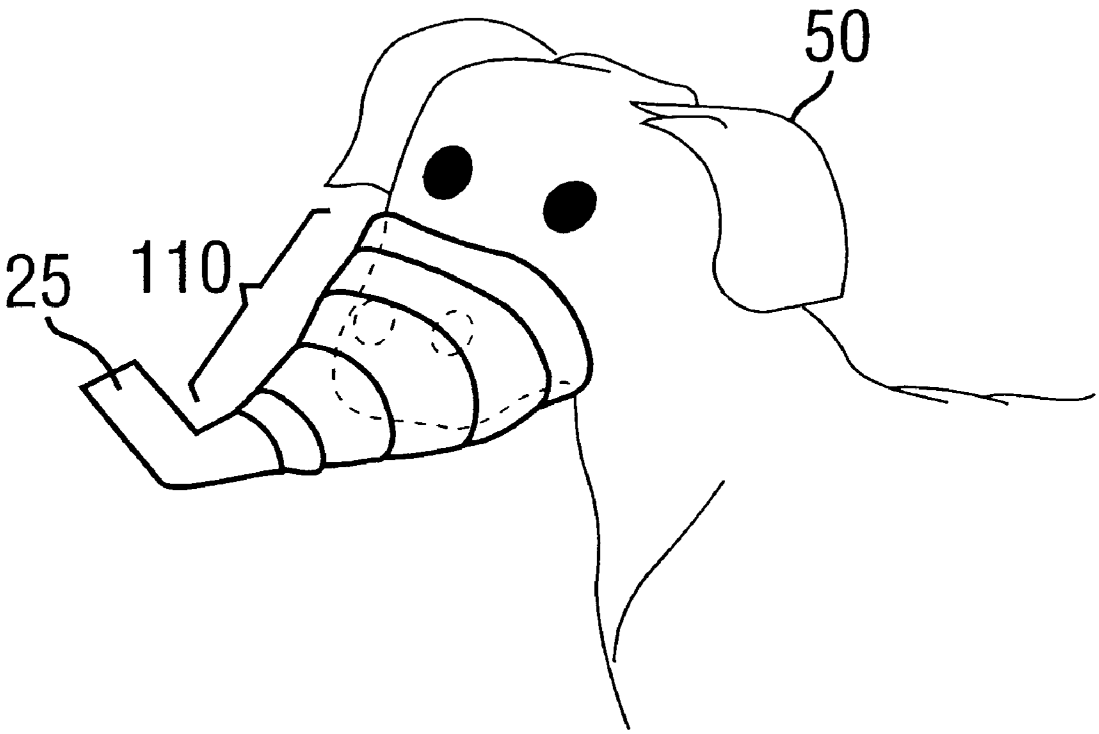
FIG. 4B shows a mask of the invention, positioned over the muzzle of an animal.

FIG. 4A shows an animal 40 (horse) with the mask 110 positioned over one of its nostrils. FIG. 4B shows an animal 50 (dog) with the mask positioned over the muzzle of the animal. When applied to large animals, in particular to horses, the mask is preferably positioned over one nostril only. It has been found in practice, that a horse has sufficient vacuum in one nostril when it breathes in (without having to block up the other nostril) to effect the suitable medicament flow from delivery device 25.

The device 25 may be used for any drug formulation which may be advantageously administered to the lung or nasal passages in an animal, to cure or alleviate any illness or its symptoms. Typical illnesses include COPD, asthma, allergy, etc . . . , and suitable drugs include β-agonists or antagonists, steroids eg., beclomethasone, fluticasone or budesonide, anti-cholinergics e.g., ipratropium bromide, etc . . . Therapeutically effective formulations and dosages to be administered using the devices described herein are well known to practitioners. One of skill will appreciate that practitioners may opt to aker dosages and/or formulations to fit a particular patient/animal needs.

Figure 5:
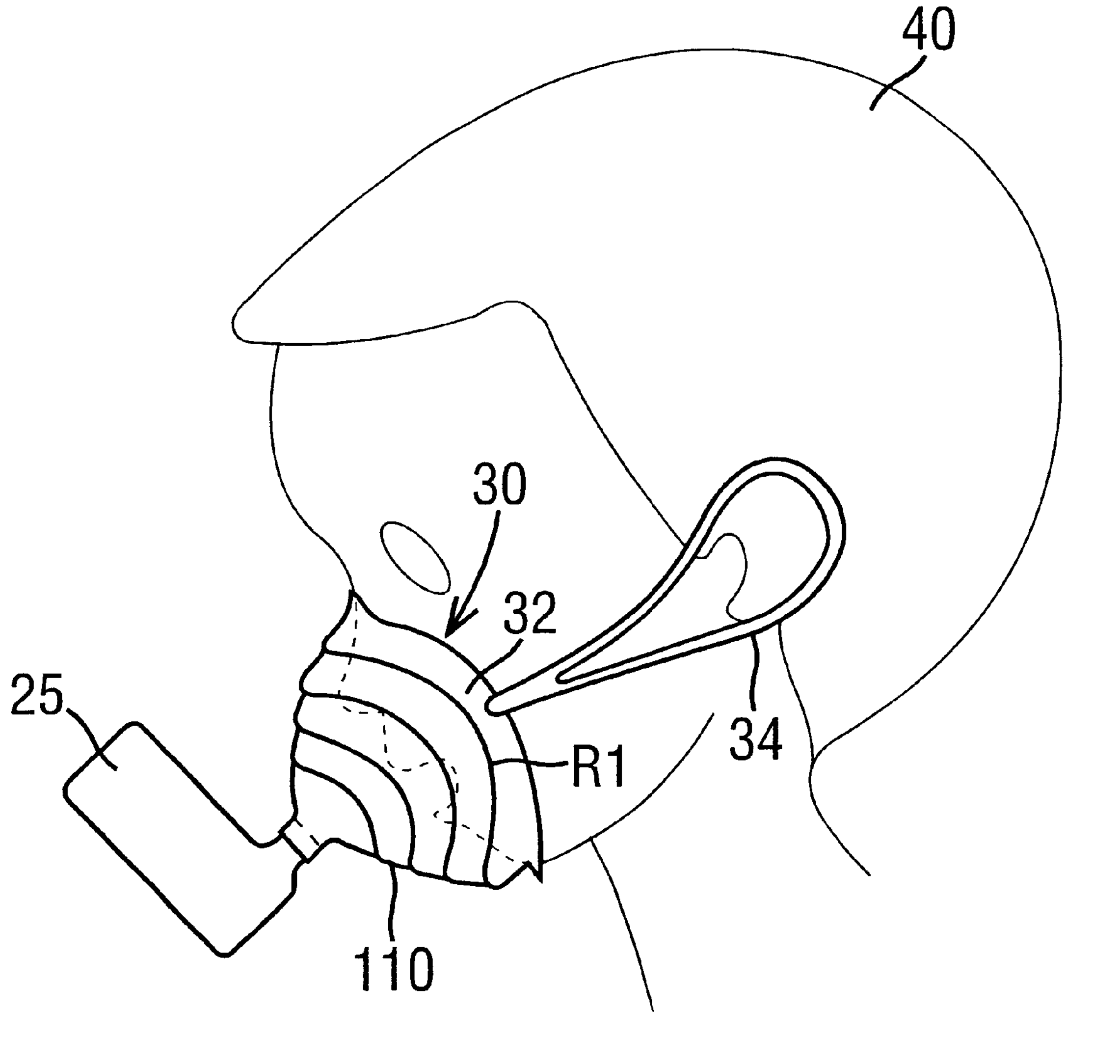
FIG. 5 shows in diagrammatic form, an exemplary drug delivery mask of the invention, in an open state as it might be deployed over the head of a small human child.
Figure 6:
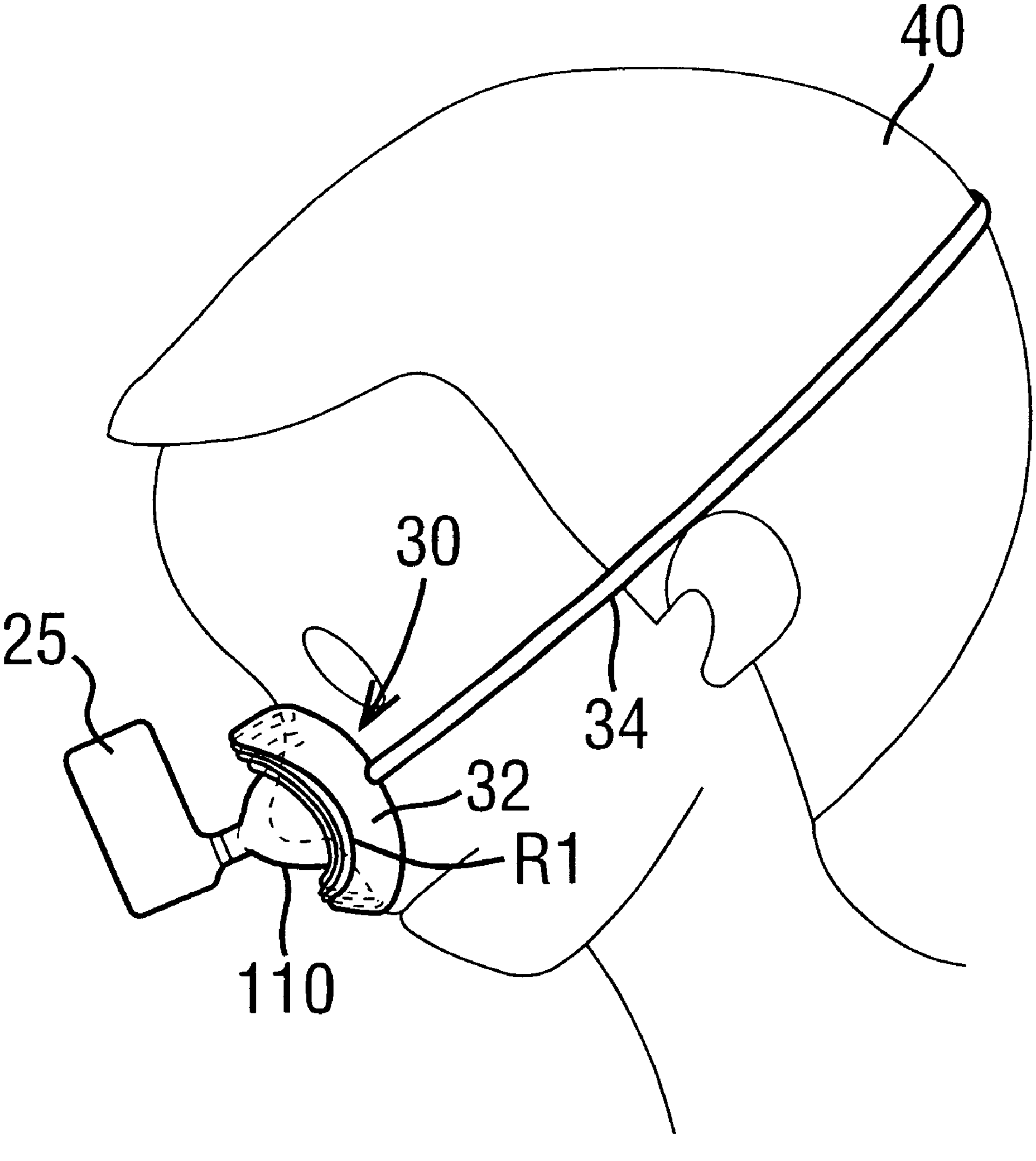
FIG. 6 shows in diagrammatic form, an exemplary drug delivery mask of the invention, in an open state as it might be deployed in collapsible form over the nose of a small human child.

An exemplary drug delivery mask 110 showing the use of the invention for humans 40, is shown in diagrammatic form in FIGS. 5 and 6. The mask of FIG. 5 includes all the characteristics described above but is especially adapted for human use.

The mask 110 is a unitary structure. FIG. 5 shows the mask 110 in an open state, having a bell or similar shape, as it might be deployed over the nostrils and mouth of a small child 40 in use. In various embodiments, the dispenser 25 may be a metered dose breath-actuated. or user—(e.g., care giver) operated inhaler and may be a dry powder or aerosol dispenser. In other embodiments, the sheet 32 can be in the form of a conic-frustum shaped shroud made of an easily stretchable elastic material and/or highly flexible material. The sheet 32 is adapted to provide a substantial (although not necessarily total) pneumatic seal between ring R1 and the nostrils and/or mouth of a human 40. As illustrated in phantom in FIGS. 5 and 6, the interface 30 may optionally include a stretchable elastic or otherwise adjustable strap 34 extending from or near opposite sides of ring R1, to permit secure fixture of mask 110 to the front of the face (mouth and/or nostrils) of a human 40. The mask may fit over either the nostrils or the mouth separately. It should be understood, however, that the mask 110 can be used without the strap 34 or with a different type of strap(s).

FIG. 6 illustrates the mask 110 used in a partially open form, where one of the rings R1 forms the necessary seal around the nose of a human 40. In this way, a single mask 110 may accommodate various sizes of the front of the face (mouth and/or nostrils) of a human 40.

Figure 7:
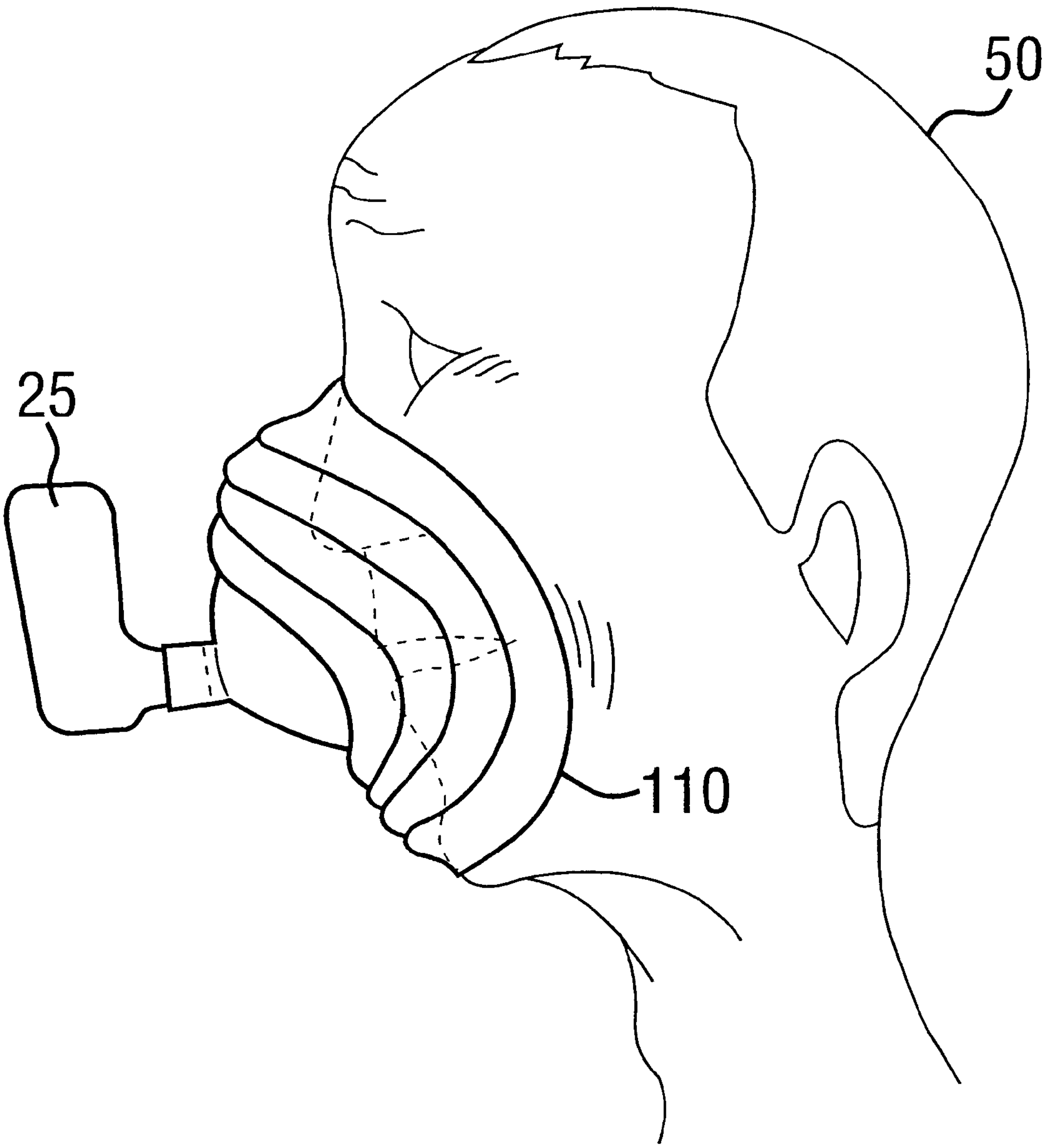
FIG. 7 shows in diagrammatic form, an exemplary drug delivery mask of the invention, in an open state as it might be deployed over the head of a human adult.

FIG. 7 shows a human 50 (human adult or elderly person) with the mask 110 positioned over the nostrils and mouth of the human 50. The mask 110 in this figure may also fit over either the nostrils or the mouth separately. The device 25 may be used for any drug formulation that may be advantageously administered to the lung or nasal passages in a human 50 or 40, to cure or alleviate any illness or its symptoms. Typical illnesses include COPD, asthma, allergy, etc . . . , and suitable drugs include β-agonists or antagonists, steroids e.g., beclomethasone, fluticasone or budesonide, anti-cholinergics e.g., ipratropium bromide, etc . . . The doses for children may be the same or similar to those used to treat adult diseases or may be increased or decreased or given in multiple applications as dependant on the size of the human.

Figure 8A:
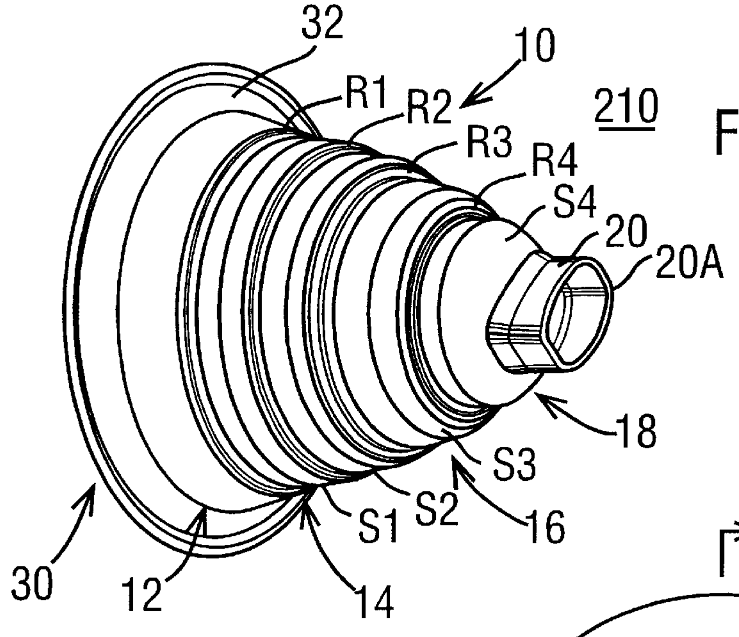
FIG. 8A shows a perspective view of another drug delivery mask in accordance with the invention.
Figure 8B:
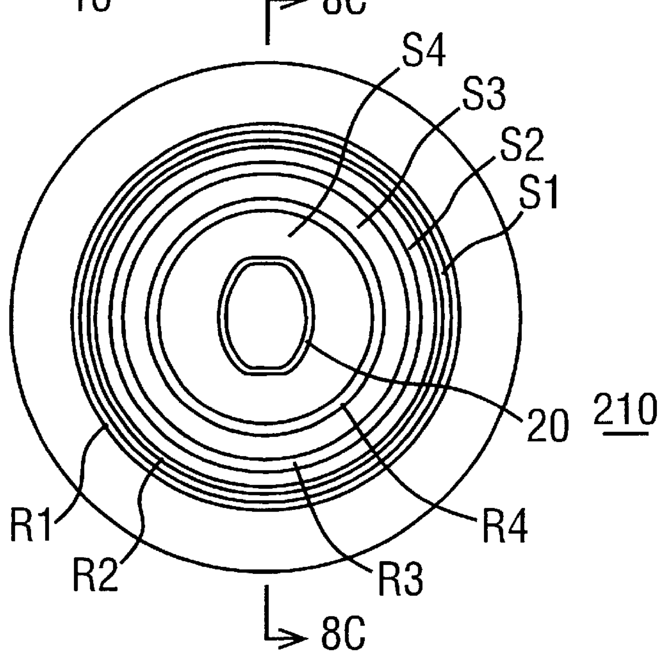
FIG. 8B shows an end plan view of the mask of FIG. 8A.
Figure 8C:
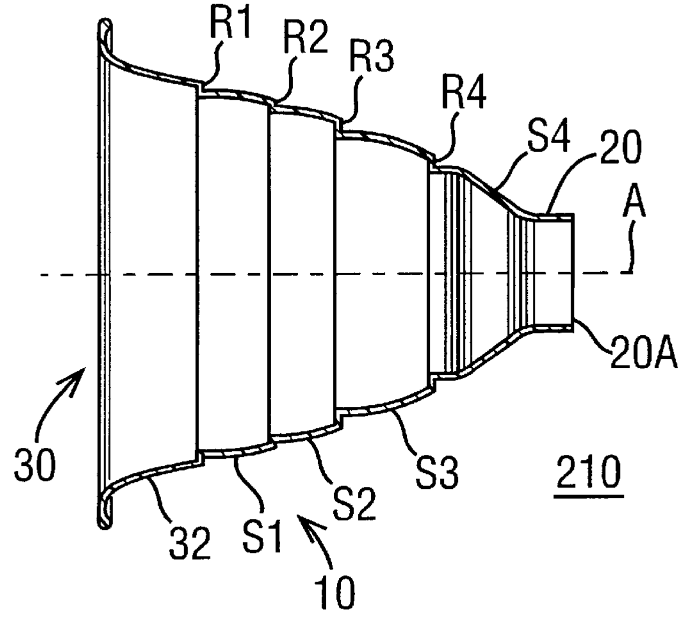
FIG. 8C shows a sectional view of the mask taken along line 8C—8C of FIG. 8B.
Figure 8D:
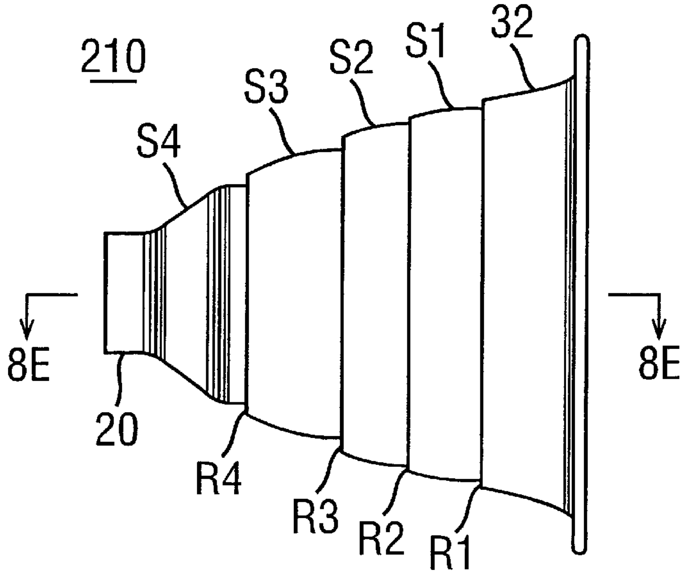
FIG. 8D shows a side elevation view of the mask of FIG. 8A.
Figure 8E:
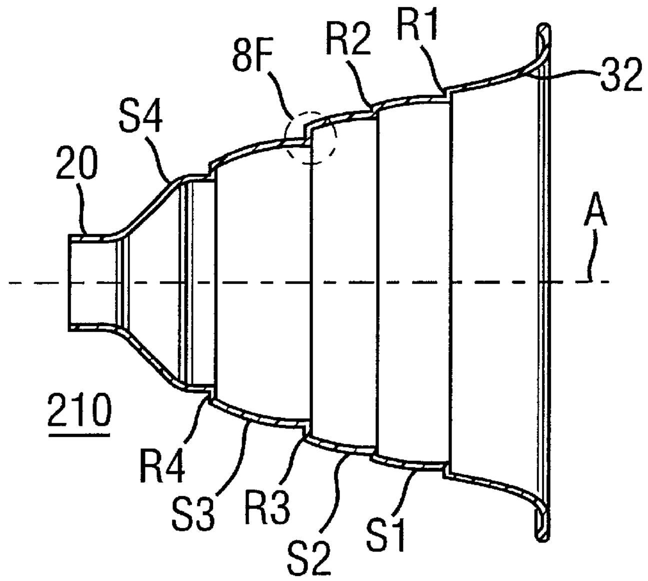
FIG. 8E shows a sectional view of the mask taken along line 8E—8E of FIG. 8D.
Figure 8F:
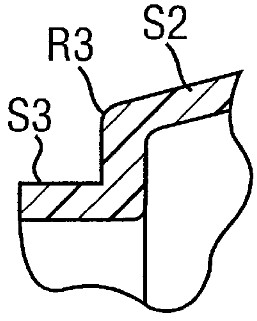
FIG. 8F shows an enlarged sectional view of a portion of the mask contained in circle 8F of FIG. 8E.
Figure 8G:
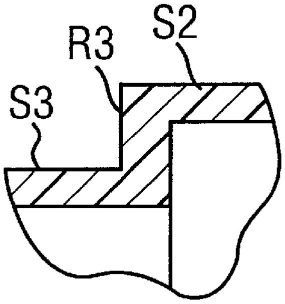
FIG. 8G shows an enlarged sectional view, similar to FIG. 8F, of another mask.
Figure 8H:
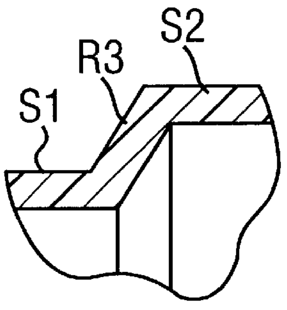
FIG. 8H shows an enlarged sectional view, similar to FIG. 8F, of another mask.

FIGS. 8A–8E show an additional mask 210 according to the present invention. The mask 210 is similar to the mask 110 of FIGS. 1 through 3, such that elements that are the same have the same reference numerals. As also shown in FIG. 8F, the rings R1, R2, R3, and R4 of the mask 210 each have a four-sided cross-section transverse to the axis "A" instead of a C-shaped cross-section. The. cross-section of the ring R3 of FIG. 8F is a trapazoid that extends transversed to the axis "A". The rings Ri can each have alternative cross-sections including a rectangular cross-section that extends transversed to the axis "A" as shown in FIG. 8G, or a rectangular cross-section that extends at an angle to the axis "A" as shown in FIG. 8H. Many variations of the ring Ri are possible under the scope of the present invention.

Figure 9:
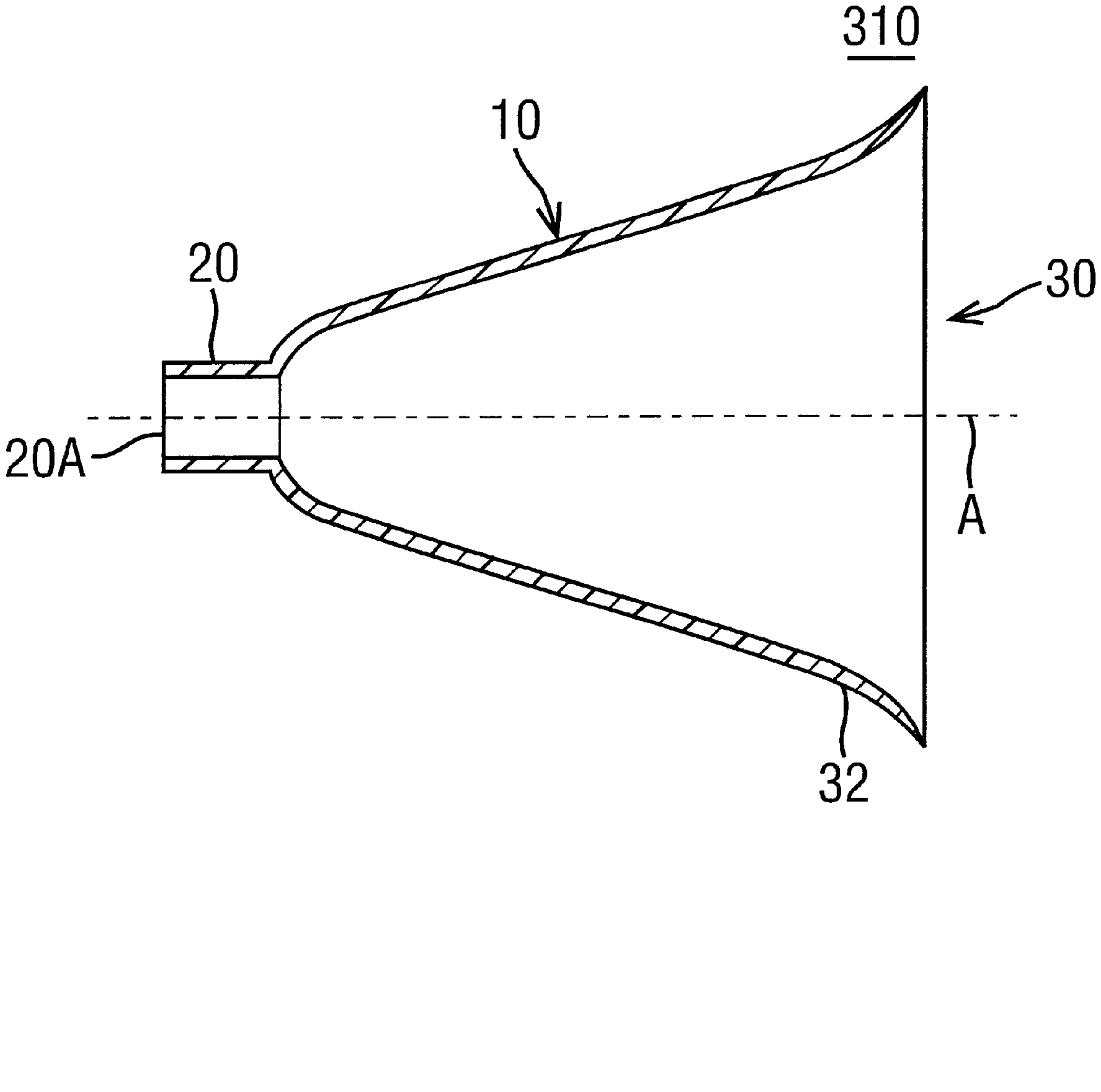
FIG. 9 shows a sectional view of a further drug delivery mask in accordance with the invention.

FIG. 9 shows a further mask 310 according to the present invention. The mask 310 is similar to the mask 110 of FIGS. 1 through 3, such that elements that are the same have the same reference numerals. The sleeve 10 of the mask 310, however, does not include the different multiple rings and skirts of the mask 110 of FIGS. 1 through 3. The mask 310 is, in effect, a more simple embodiment of the present invention, and includes the airborne medicament interface adapter 20, the mammal interface adapter 30, and the relatively flexible sleeve extending along the axis "A" between the medicament interface adapter and the mammal interface adapter. The sleeve 10 has a cross sectional monotonically increasing between the medicament interface adapter and the mammal interface adapter.

EXAMPLE I

Pediatric Use of the Drug Delivery Mask

To illustrate the effectiveness of a representative embodiment of the invention, the device shown in FIG. 2 is used to administer various medications to a group of human patients between the age of 0–17. In the case of medications requiring pulmonary or nasal absorption, the mask is held in place over the nostrils and/or the mouth and against the face of the patient being treated. In the case of medications specifically requiring nasal absorption the mask is placed over both nostrils (see FIG. 6). In the case of pulmonary medicaments, blood plasma analysis will reveal concentrations levels of the administered medications consistent with pulmonary absorption. In the case of medicaments which are nasally absorbed, effective delivery will be confirmed by observing an ascertainable improvement in the patients symptoms.

EQUIVALENTS

While the claimed invention has been described in detail and with reference to specific embodiments thereof, it will be apparent to one of ordinary skill in the art that various changes and modifications can be made to the claimed invention without departing from the spirit and scope thereof. Thus, for example those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A drug delivery device for removable fixture to an animal, comprising:

A. an airborne medicament interface adapter adapted to couple to a medicament dispenser in a sealed manner;

B. an animal interface adapter adapted to establish a substantial seal between the animal interface adapter and the animal; and C. a relatively flexible sleeve extending along an axis between the medicament interface adapter and the animal interface adapter, and having a cross sectional monotonically increasing between the medicament interface adapter and the animal interface adapter, wherein the relatively flexible sleeve comprises at least two sections extending along the axis, each of the sections including a relatively inflexible ring defining an associated first contour, and a relatively flexible skirt extending from the ring to a distal edge defining an associated second contour, wherein the rings are nestable, forming a succession of monotonically decreasing sized rings from a largest ring to a smallest ring, and wherein the second contour of the skirt of each ring in the succession, is substantially the same as, and is joined to, the first contour of the next smaller ring in the succession;

wherein the medicament interface adapter extends from the distal edge of the skirt of smallest ring; and wherein the animal interface adapter extends from the largest ring.

2. A device according to claim 1, further comprising a medicament dispenser coupled to the airborne medicament interface adapter.

3. A device according to claim 2, wherein the dispenser is a breath actuated dispenser.

4. A device according to claim 3, wherein the dispenser is an aerosol dispenser.

5. A device according to claim 3, wherein the dispenser is a dry powder dispenser.

6. A device according to claim 2, wherein the medicament dispenser is operable by a user.

7. A device according to claim 1, wherein the sleeve is made from one of the group consisting of a thermoplastic elastomer, high density polyethylene, low density polyethylene, polypropylene, silicone, rubber and synthetic rubber.

8. A device according to claim 1, wherein the animal interface adapter and the largest ring are joined by one of the group consisting of co-molding, gluing, mechanical fixing, and ultrasonic welding.

9. A device according to claim 1, wherein the animal interface adapter includes a strap extending therefrom and adapted to secure the animal interface adapter against the animal.

10. A device according to claim 1, wherein the animal interface adapter is adapted to establish a substantial seal between the animal interface adapter and an animal comprising a horse.

11. A device according to claim 1, wherein the animal interface adapter is adapted to establish a substantial seal between the animal interface adapter and an animal comprising a human.

12. A device according to claim 1, wherein at least one of the relatively inflexible rings has a four-sided cross-section transverse to the axis.

13. A device according to claim 1, wherein at least one of the relatively inflexible rings has a C-shaped cross-section transverse to the axis.

14. A device according to claim 1, wherein the relatively inflexible rings have a wall thickness greater than a wall thickness of the relatively flexible skirts.

15. A device according to claim 1, wherein the airborne medicament interface adapter has a generally circular axial cross-section.

16. A device according to claim 1, wherein the animal interface adapter has a generally circular axial cross-section.

17. A device according to claim 1, wherein the sleeve has a generally circular axial cross-section.

18. A device according to claim 1, wherein said animal interface adapter is adapted to establish said seal to be about a single nostril of said animal.

19. A drug delivery device for removable fixture to an animal, comprising:

A. a relatively flexible sleeve extending along an axis between a proximal end and a distal end, and having a cross section increasing between the proximal end and the distal end, wherein the sleeve comprises at least two sections extending along the axis, each of the sections including a relatively inflexible ring defining an associated first contour, and a relatively flexible skirt extending in a monotonically decreasing manner from the ring to a distal edge defining an associated second contour, forming a succession of decreasing sized rings from a largest ring to a smallest ring, and wherein the second contour of the skirt of each ring in the succession, is substantially the same as, and is joined to, the first contour of the next smaller ring in the succession;

B. an airborne medicament interface adapter extending from the distal edge of the skirt of the smallest ring, wherein the medicament interface adapter is adapted to couple to a medicament dispenser in a sealed manner; and C. an animal interface adapter extending from the largest ring, wherein the animal interface adapter is adapted to establish a substantial seal between the animal interface adapter and the animal.

20. A device according to claim 19 further comprising a medicament dispenser coupled to the airborne medicament interface adapter.

21. A device according to claim 20, wherein the dispenser is a breath actuated dispenser.

22. A device according to claim 21, wherein the dispenser is an aerosol dispenser.

23. A device according to claim 21, wherein the dispenser is a dry powder dispenser.

24. A device according to claim 20, wherein the medicament dispenser is operable by a user.

25. A device according to claim 19, wherein the sleeve is made, from one of the group consisting of a thermoplastic elastomer, high density polyethylene, low density polyethylene, polypropylene, silicone, rubber and synthetic rubber.

26. A device according to claim 19, wherein said animal interface adapter and the largest ring are joined by one of the group consisting of co-molding, gluing, mechanical fixing, and ultrasonic welding.

27. A device according to claim 19, wherein the animal interface adapter includes a strap extending therefrom and adapted to secure the animal interface adapter against the animal.

28. A device according to claim 19, wherein the animal interface adapter is adapted to establish a substantial seal between the animal interface adapter and an animal comprising a horse.

29. A device according to claim 19, wherein the animal interface adapter is adapted to establish a substantial seal between the animal interface adapter and an animal comprising a human.

30. A device according to claim 19, wherein at least one of the relatively inflexible rings has a four-sided cross-section transverse to the axis.

31. A device according to claim 19, wherein at least one of the relatively inflexible rings has a C-shaped cross-section transverse to the axis.

32. A device according to claim 19, wherein the relatively inflexible rings have a wall thickness greater than a wall thickness of the relatively flexible skirts.

33. A device according to claim 19, wherein the airborne medicament interface adapter has a generally circular axial cross-section.

34. A device according to claim 19, wherein the animal interface adapter has a generally circular axial cross-section.

35. A device according to claim 19, wherein the sleeve has a generally circular axial cross-section.

36. A device according to claim 19, wherein said animal interface adapter is adapted to establish said seal to be about a single nostril of said animal.

37. A device according to claim 19, wherein said rings are nestable.

* * * * *